United States Patent [19]

Chan

[11] Patent Number: 5,679,549
[45] Date of Patent: Oct. 21, 1997

[54] PRODUCTION OF RECOMBINANT FACTOR VIII IN THE PRESENCE OF LIPOSOME-LIKE SUBSTANCES OF MIXED COMPOSITION

[75] Inventor: Sham-Yuen Chan, El Sobrante, Calif.

[73] Assignee: Bayer Corporation, Berkeley, Calif.

[21] Appl. No.: 434,900

[22] Filed: May 4, 1995

[51] Int. Cl.$^6$ ..................................................... C12P 21/02
[52] U.S. Cl. .......................... 435/69.6; 435/172.3; 530/383
[58] Field of Search ............................... 435/69.6, 240.2, 435/172.3; 530/383

[56] References Cited

U.S. PATENT DOCUMENTS 5,198,349  3/1993  Kaufman ............................ 435/69.6

Primary Examiner—Robert A. Wax
Assistant Examiner—Enrique D. Longton
Attorney, Agent, or Firm—James A. Giblin; Michael J. Beck

[57] ABSTRACT

Recombinant Factor VIII expression in a mammalian cell culture can be increased by including a novel liposome-like substance in the culture medium. The liposome-like substance comprises at least two (preferably at least three) different lipids in defined molar ratios. In a preferred embodiment, the addition of a liposome-like substance comprised of dioleoyl phosphatidylcholine, phosphatidylethanolamine, and phosphatidylserine in a molar ratio of 4:1:1 to the culture medium of GS-MDR cells resulted in an increase in FVIII production by a factor greater than five.

2 Claims, No Drawings

PRODUCTION OF RECOMBINANT FACTOR VIII IN THE PRESENCE OF LIPOSOME-LIKE SUBSTANCES OF MIXED COMPOSITION

BACKGROUND OF THE INVENTION

1. Field

This disclosure is concerned generally with the production of recombinant Factor VIII in a mammalian cell expression system. Specifically, the disclosure relates to the addition of a liposome-like substance containing lipids in defined ratios to the mammalian cell culture medium to increase yields of recombinant Factor VIII.

2. Background

Factor VIII is a plasma protein required for normal hemostasis, or clotting of the blood. Functional Factor VIII is lacking in individuals with hemophilia A because of a mutation in the gene encoding this protein, which is located in the X-chromosome. To control bleeding episodes, hemophiliacs must be treated with Factor VIII, which historically has been isolated from human blood plasma.

The human Factor VIII gene encompasses 186,000 base pairs and constitutes 0.1% of the entire X-chromosome, making it among the largest genes known (1). The transcription product of this gene, which is derived from 26 exons, is a messenger RNA molecule of ~9000 bases in length, coding for a large protein of 2351 amino acids. Structural studies of Factor VIII indicate that it is a glycoprotein, containing a significant number of carbohydrate residues. The cDNA coding for Factor VIII has been cloned (2,3) and stably expressed in baby hamster kidney cells (BHK-21) (3) and Chinese hamster ovary cells (4). The availability of these high producing cell clones has made large-scale production of recombinant Factor VIII (rFVIII) feasible. Two significant challenges in the commercial production of rFVIII are (i) the development of a serumfree medium that will support high density cultures and stabilize rFVIII, and (ii) an efficient purification scheme that will yield high purity rFVIII.

Previously it has been demonstrated that the addition of bovine lipoprotein or human low density lipoprotein to serumfree cultures significantly improve the productivity of recombinant BHK-21 and human embryonic kidney (293S) cells expressing rFVIII (5). The co-expression of vonWillebrand factor and the addition of phospholipids to serumfree medium have been shown to be effective in enhancing the stability of rFVIII produced by rFVIII expressing CHO cells (6).

I have found that certain liposome-like substances comprising at least two (preferably at least three) lipids can be used as culture supplements in the serumfree production of rFVIII. Contrary to the prior art (6), I have observed that certain liposome-like substances comprised of lipids such as phosphatidylcholine (PC), phosphatidylethanolamine (PE), or phosphatidylserine (PS) alone have no effect on rFVIII expression in BHK-21 and 293S cells. However, liposome-like substances comprising combinations of different lipids, such as cholesterol, fatty acids such as linoleic acid and palmitic acid, PC, PE, and PS, at certain ratios were found to have a significant enhancing effect on rFVIII expression in BHK-21 and 293S cells. A serumfree production medium for long term production of rFVIII was developed from these new findings.

SUMMARY OF THE INVENTION

I have found a method and medium for substantially increasing the productivity of a mammalian cell expression system producing recombinant Factor VIII by a factor greater than about four. The essential step of the method consists of the addition of a liposome-like substance to the cell growth medium of the expression system. As used herein, "liposome-like substance" means vesicles or other tertiary-structures comprising one or more bilayers comprised of at least two different lipids in fixed molar ratios. Molar ratios should be understood to be approximate.

This invention is illustrated in the following examples, which set forth typical procedures and cell culture media for production (preferably continuous production) of rFVIII using the liposome-like substances to deliver lipid supplements to recombinant cells expressing high levels of rFVIII.

SPECIFIC EMBODIMENTS

Preparation of Liposome-Like Substances

All synthetic phospholipids were obtained from Avanti Polar Lipids, Inc. (Alabaster, Ala.). Phospholipids were delivered as $0.1\mu$ liposome-like substances. Lyophilized phospholipids were reconstituted in 50 mM Tris-150 mM NaCl (pH 7.4) and extruded through a $0.1\mu$ polycarbonate membrane with the aid of a hand-held device—LiposoFast (Avestin, Inc., Ottawa, Canada). The sized liposome-like substances were then filtered with a $0.2\mu$ filter and added aseptically to culture medium. Phosphatidylethanolamine (PE), phosphatidylcholine (PC), and phosphatidylserine (PS) were examined either as single components or mixtures. Other lipids such as cholesterol and free fatty acids were also incorporated into the liposome-like substances.

EXAMPLE I

Effect of Various Lipid Mixtures on the Expression of rFVIII in 293S Cells

GS-10 (recombinant 293S cells expressing high levels of Factor VIII) cells were maintained as serumfree cultures in shake flasks using a serumfree medium (Dulbecco's minimum essential medium and F12 at a ratio of 1:1, obtained from Life Technologies, Bethesda, Md.) supplemented with insulin (10 µg/ml) and transferrin (25 µg/ml). Long term evaluation was done in shake flasks with an initial seeding density of $3\times10^6$ cells/ml. Complete medium exchanges were done at 24-hour intervals where cells were spun, washed and reseeded at $3\times10^6$ cells/ml. A typical shaker culture contains 25–50 ml of cells. Factor VIII activity was determined by Coatest VIII (Kabi Pharmacia, Franklin, Ohio), a chromogenic assay, according to manufacturer's instructions.

The initial screening of phospholipids was done using 24-hour plate cultures. After determining the optimal ratio of various phospholipids, the study was then confirmed in shake flasks over a period of 10–14 days. As shown in Table 1, while PC and PE alone had no effect on Factor VIII expression, PS alone was found to be inhibitory. By combining PC, PS, and PE at various ratios, significant increases in Factor VIII expression were observed. The highest productivity was observed in cells supplemented with PC:PE:PS (4:1:1), PC:PS:cholesterol (8:1:1), and PC:PS:palmitic acid:linoleic acid (7:3:0.5:0.5). The optimal concentration of phospholipids was found to be 30 µg/ml. The optimal length of the acyl side chain of various phospholipids was determined to be C18. All optimization studies were subsequently done with dioleoyl phospholipids.

EXAMPLE II

Expression of Factor VIII in Continuous Culture

I measured the effect of various liposome-like substances on the production of factor VIII in long term shake flask cultures with PC:PE:PS (4:1:1), PC:PS: palmitic acid:linoleic acid (7:3:0.5:0.5), and PC:PS:cholesterol (8:1:1). The culture conditions were done as described in Example I. The concentration of the liposome-like substances was at 30 µg/ml. Complete medium exchange was done at 24-hour intervals. Results are shown in Table 2.

CONCLUSION

We have demonstrated that lipid mixtures, when delivered in the form of liposome-like substances, significantly enhance the production of Factor VIII in recombinant cells. These liposome-like substances can be used as medium supplements to support production of Factor VIII, preferably continuous production of Factor VIII.

The above examples are intended to illustrate the invention and it is thought variations will occur to those skilled in the art. Accordingly, it is intended that the scope of the invention should be limited only by the claims below.

TABLE 1

Effect of phospholipid on the expression of Factor VIII in GS-MDR cells

| Phospholipids | FVIII Titer (U/ml) |
| --- | --- |
| Dioleoyl PC/PS (7:3) | 2.8 |
| Dioleoyl PC/PS (8:2) | 2.5 |
| Dioleoyl PC/PS (9:1) | 1.4 |
| Dioleoyl PC/PS/palmitic/linoleic acid (7:3:0.5:0.5) | 3.4 |
| Dioleoyl PC/PE/PS (4:1:1) | 3.5 |
| Dioleoyl PC/PE/PS (8:1:1) | 1.7 |
| Dioleoyl PC/PE/PS (16:1:2) | 2.1 |
| Dioleoyl PC | 0.65 |
| Dioleoyl PE | 0.55 |
| Dioleoyl PS | 0.15 |
| Saline | 0.60 |

TABLE 2

Production of Factor VIII in continuous cultures of GS-10 cells

| | FVIII titer (U/ml) | | | |
| --- | --- | --- | --- | --- |
| Days | PC/PE/PS (4:1:1) | PC/PS/pm/ln (7:3:0.5:0.5) | PC/PS/Cholesterol (8:1:1) | Medium only |
| 1 | 2.44 | 2.51 | 2.41 | 0.35 |
| 2 | 2.78 | 2.89 | 2.72 | 0.4 |
| 3 | 2.46 | 2.77 | 2.69 | 0.44 |
| 4 | 2.82 | 2.8 | 2.7 | 0.48 |
| 5 | 2.88 | 2.95 | 2.99 | 0.42 |
| 6 | 2.9 | 3.1 | 2.95 | 0.41 |
| 7 | 3.21 | 3.18 | 3.12 | 0.54 |
| 8 | 3.18 | 3.22 | 3.06 | 0.55 |
| 9 | 3.02 | 3.16 | 3.14 | 0.58 |
| 10 | 3.34 | 3.38 | 3.27 | 0.53 |
| 11 | 2.97 | 3.15 | 3.19 | 0.49 |
| 12 | 3.12 | 2.95 | 2.98 | 0.52 |
| 13 | 3.02 | 3.12 | 2.71 | 0.54 |
| 14 | 2.89 | 3.16 | 3.22 | 0.56 |
| 15 | 3.22 | 3.38 | 3.34 | 0.51 | pm = palmitic acid
ln = linoleic acid

REFERENCES

1. Gitschier el al. 1984 Nature 312: 326–329
2. Wood et al. 1984 Nature 312: 330–337
3. Toole et al. 1984 Nature 312: 342–347
4. Kaufman et al. 1989 Mol. Cell Biol. 9: 1233–1242
5. Chan el al. 1991 In Vitro 27: 121
6. Kaufman et al. 10/1993 U.S. Pat. No. 5,250,421

What is claimed is:

1. A method for increasing the production level of recombinant factor VIII in a mammalian cell culture expression system by at least fourfold, comprising the step of adding to the culture system fixed molar ratios of a mixture of synthetic lipids in the form of a liposome-like substance selected from the group consisting of phosphatidylcholine, phosphatidylethanolamine and phosphatidylserine in a molar ratio of about 4:1:1, phosphatidylcholine, phosphatidylserine and cholesterol in molar ratio of about 8:1:1 and phosphatidylcholine, phosphatidylserine, palmitic acid and linoleic acid in a molar ratio of about 7:3:0.5:0.5 under conditions sufficient to assure the fourfold increase in productivity.

2. A cell culture medium containing fixed molar ratios of a mixture of synthetic lipids in the form of liposome-like substance, wherein said liposome-like substance is selected from the group consisting of phosphatidylcholine, phosphatidylethanolamine and phosphatidylserine in a molar ratio of about 4:1:1, phosphatidylcholine, phosphatidylserine and cholesterol in a molar ratio of about 8:1:1 and phosphatidylcholine, phosphatidylserine, palmitic acid and linoleic acid in a molar ratio of about 7:3:0.5:0.5 sufficient to assure a fourfold increase in factor VIII expression in a mammalian cell culture system.

* * * * *